(12) United States Patent
Horton et al.

(10) Patent No.: US 9,801,736 B2
(45) Date of Patent: Oct. 31, 2017

(54) ALIGNMENT DEVICE FOR A PROSTHETIC LEG LINER PIN

(71) Applicants: Lee A. Horton, Jefferson, MA (US); Leslie J. Horton, Jefferson, MA (US)

(72) Inventors: Lee A. Horton, Jefferson, MA (US); Leslie J. Horton, Jefferson, MA (US)

(*) Notice: Subject to any disclaimer, the term of this patent is extended or adjusted under 35 U.S.C. 154(b) by 0 days.

(21) Appl. No.: 15/465,900

(22) Filed: Mar. 22, 2017

(65) Prior Publication Data

US 2017/0189209 A1    Jul. 6, 2017

Related U.S. Application Data

(63) Continuation of application No. 14/157,771, filed on Jan. 17, 2014, now abandoned.

(60) Provisional application No. 61/754,073, filed on Jan. 18, 2013.

(51) Int. Cl.
*A61F 2/76* (2006.01)
*A61F 2/78* (2006.01)

(52) U.S. Cl.
CPC .............. *A61F 2/76* (2013.01); *A61F 2/7812* (2013.01); *A61F 2002/7868* (2013.01); *A61F 2002/7875* (2013.01)

(58) Field of Classification Search
CPC ...... A61F 2/60; A61F 2/76; A61F 2/78; A61F 2/7812; A61F 2/7856; A61F 2/80; A61F 4/00; A61F 2002/7818; A61F 2002/7825; A61F 2002/7831; A61F 2002/7837; A61F 2002/7868; A61F 2002/7856; A61F 2002/7881; A61F 2002/7893; A47G 21/08; A47G 25/80; A47G 25/90; A47G 25/904; A47G 25/905; A47G 25/908
See application file for complete search history.

(56) References Cited

U.S. PATENT DOCUMENTS

| | | | |
|---|---|---|---|
| 5,503,543 | A | 4/1996 | Laghi |
| 5,885,509 | A | 3/1999 | Kristinsson |
| 5,888,234 | A | 3/1999 | Littig |
| 6,051,026 | A | 4/2000 | Biedermann et al. |
| 6,102,262 | A | 8/2000 | Nicholson |
| 6,440,173 | B1 | 8/2002 | Meyer |
| 6,536,636 | B1 | 3/2003 | McDonniel |
| 7,438,843 | B2 | 10/2008 | Asgeirsson |
| 7,662,191 | B2 | 2/2010 | Asgeirsson |
| 2002/0042659 | A1 | 4/2002 | Ingimarsson |
| 2007/0221101 | A1 | 9/2007 | Schiel |
| 2009/0026233 | A1 | 1/2009 | Smith |
| 2009/0120975 | A1 | 5/2009 | Schoepe |
| 2010/0147908 | A1 | 6/2010 | Skerman |

OTHER PUBLICATIONS

Alps. The Liberty II Locking Gel Liner. Feb. 17, 2011 verified by the Wayback Machine.
Zahedi. Alignment of lower-limb prostheses. Journal of Rehabilitation Research. vol. 23, No. 2. pp. 2-19. 1986.

*Primary Examiner* — Thomas J Sweet
*Assistant Examiner* — Christie Bahena
(74) *Attorney, Agent, or Firm* — Fish & Richardson P.C.

(57) ABSTRACT

A prosthetic liner and liner pin alignment device has a support, and a body extending from the support. The body has a cup defining an inner wall surface defining a liner-receiving recess having a longitudinal axis and defining a liner pin-receiving guide hole to a liner pin-receiving pin guide aperture. The liner pin-receiving pin guide aperture has a central axis parallel to the longitudinal axis of the liner-receiving recess.

22 Claims, 10 Drawing Sheets

ALIGNMENT DEVICE FOR A PROSTHETIC LEG LINER PIN

CROSS-REFERENCE TO RELATED APPLICATIONS

This application is a continuation of U.S. patent application Ser. No. 14/157,771, filed on Jan. 17, 2014, which claims priority to U.S. provisional patent application 61/754,073, filed on Jan. 18, 2013. The entire contents of the above applications are hereby incorporated by reference.

TECHNICAL FIELD

This invention relates to prosthetic leg liner pins, and more particularly to alignment devices for same.

BACKGROUND

Below-the-knee prosthetic legs are typically attached using a suspension liner that covers the amputated leg stump and includes a liner pin that then locks onto the prosthetic leg. The liner is placed on the leg stump by holding the liner pin in one hand with the liner turned inside out. The liner pin is held perpendicular and aligned straight out from the stump while another hand is used to roll the liner onto the leg stump. The result should be that the liner pin is projecting perpendicular to the stump end, leaving no air between the stump and the liner, so that the prosthetic leg can be readily attached (see, e.g., Littig U.S. Pat. No. 5,888,234 and Biedermann et al. U.S. Pat. No. 6,051,026, the complete disclosures of each of which are incorporated herein by reference). If the liner pin is not positioned correctly, the user cannot easily direct the liner pin into the locking hole of the prosthetic leg. If the pin is not aligned properly, the person must take the liner off and try again. For individuals that have amputated legs that are far down on the leg, it is very difficult to bend over and hold the liner pin perpendicular to the end of the stump. If the person is elderly or overweight, it is almost impossible to hold the pin perpendicular without help from someone else.

SUMMARY

According to one aspect of the disclosure, a prosthetic liner and liner pin alignment device comprises a support, and a body extending from the support. The body comprises a cup defining an inner wall surface defining a liner-receiving recess having a longitudinal axis and defining a liner pin-receiving guide hole to a liner pin-receiving pin guide aperture. The liner pin-receiving pin guide aperture has a central axis parallel to the longitudinal axis of the liner-receiving recess.

Implementation of this aspect of the disclosure may include one or more of the following additional features. The longitudinal axis of the liner-receiving recess is coaxial with the central axis of the pin-receiving pin guide aperture. The longitudinal axis of the liner-receiving recess is coaxial with the central axis of the pin-receiving pin guide aperture. The support is a base disposed at a predetermined angle relative to the body. The predetermined angle of the body to the base is in the range of 0 degrees to 90 degrees. The predetermined angle is about 45 degrees. The cup-shaped liner-receiving recess is 4.5 inches in diameter and 2.75 inches deep. The body, in at least a region of the liner-receiving recess, is cylindrical and defines an outer surface sized and shaped to receive there-over a portion of a prosthetic liner extending from said recess. The body is cylindrical. The predetermined angle is adjustable. The support is a handle. At least a portion of said inner wall surface defining the liner-receiving recess lies parallel to the longitudinal axis of the liner-receiving recess. At least a portion of the inner wall surface defining the liner-receiving recess lies parallel to the central axis of the pin-receiving pin guide aperture.

Advantages of this device include allowing a person using a below-the-knee prosthesis to more easily attach the prosthesis to his/her leg stump. By stabilizing and supporting the liner pin, the requirement for personal maneuverability is reduced, and aligning the liner pin with the leg stump can be accomplished successfully despite relatively reduced personal levels of, e.g., balance, dexterity, and/or ability to bend over from the waist. Advantages also include increasing the independence of the person with a below-the-knee prosthesis, by allowing him/her to independently mount and/or dismount prosthesis with limited or no assistance from others.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Below-the-knee prosthetic legs are typically attached by means of a suspension liner that covers the leg stump above the amputation and includes a liner pin that extends from the liner, generally coaxial to the leg stump, to engage and lock into the prosthetic leg.

Figure 1:
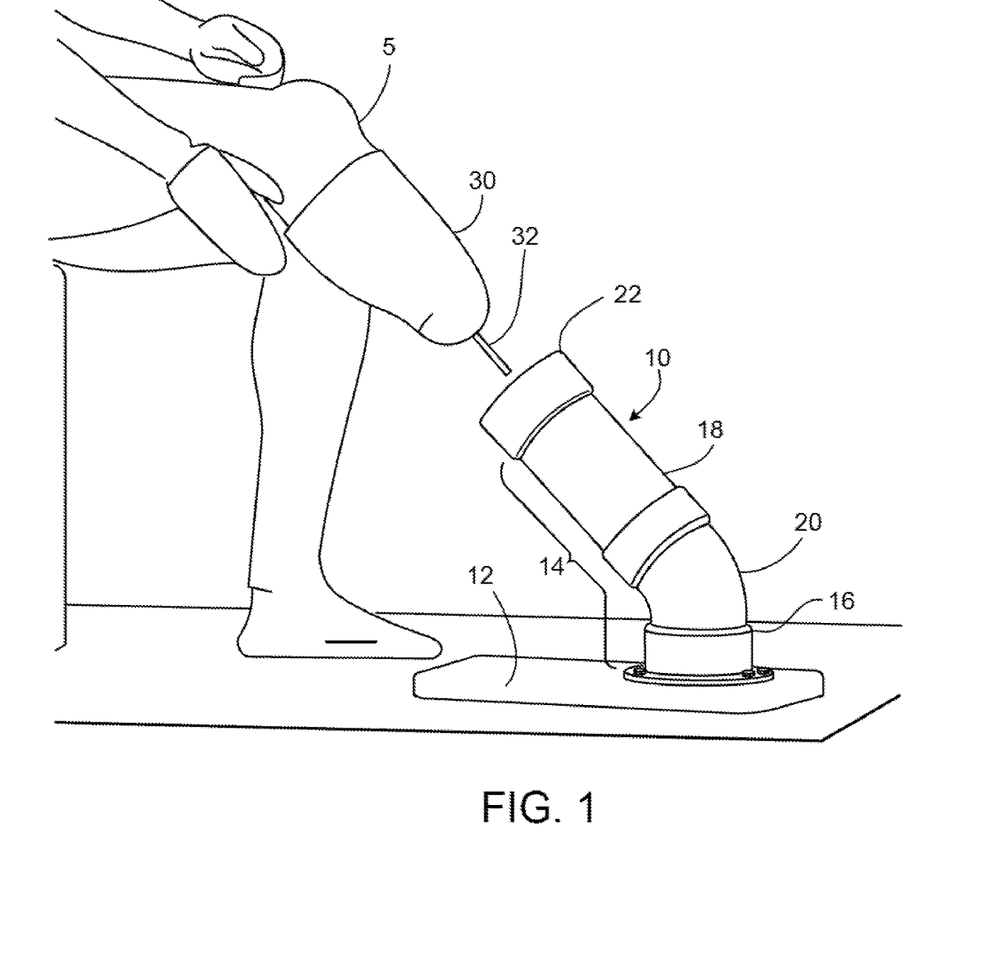
FIG. 1 is a schematic view of an alignment device of this disclosure for a prosthetic leg liner pin.

Referring to FIG. 1 et seq., the alignment device 10 is a fixture the holds the liner 30 with the liner pin 32 in proper alignment, allowing an amputee to proceed through the process of attaching a prosthetic device with the liner pin in proper position, all with limited or no assistance, and reducing the need to bend and reach, e.g. as required while trying to align the liner pin with the stump, absent availability of the alignment device 10. Referring to FIG. 1, in one implementation, the alignment device 10 has a support in the form of a base 12 that stabilizes a cylindrical guide or body 14 at a predetermined angle in an upright position on a floor surface. The cylindrical guide 14 has a vertical portion 16 and an angled portion 18 that are joined together at an angle 20. The angled portion 18 terminates at its upper end in the form of an open cup 22 defining a liner-receiving recess 23. The cup 22 has a diameter sized to receive the liner 30 and user's leg stump 5.

Figure 2:
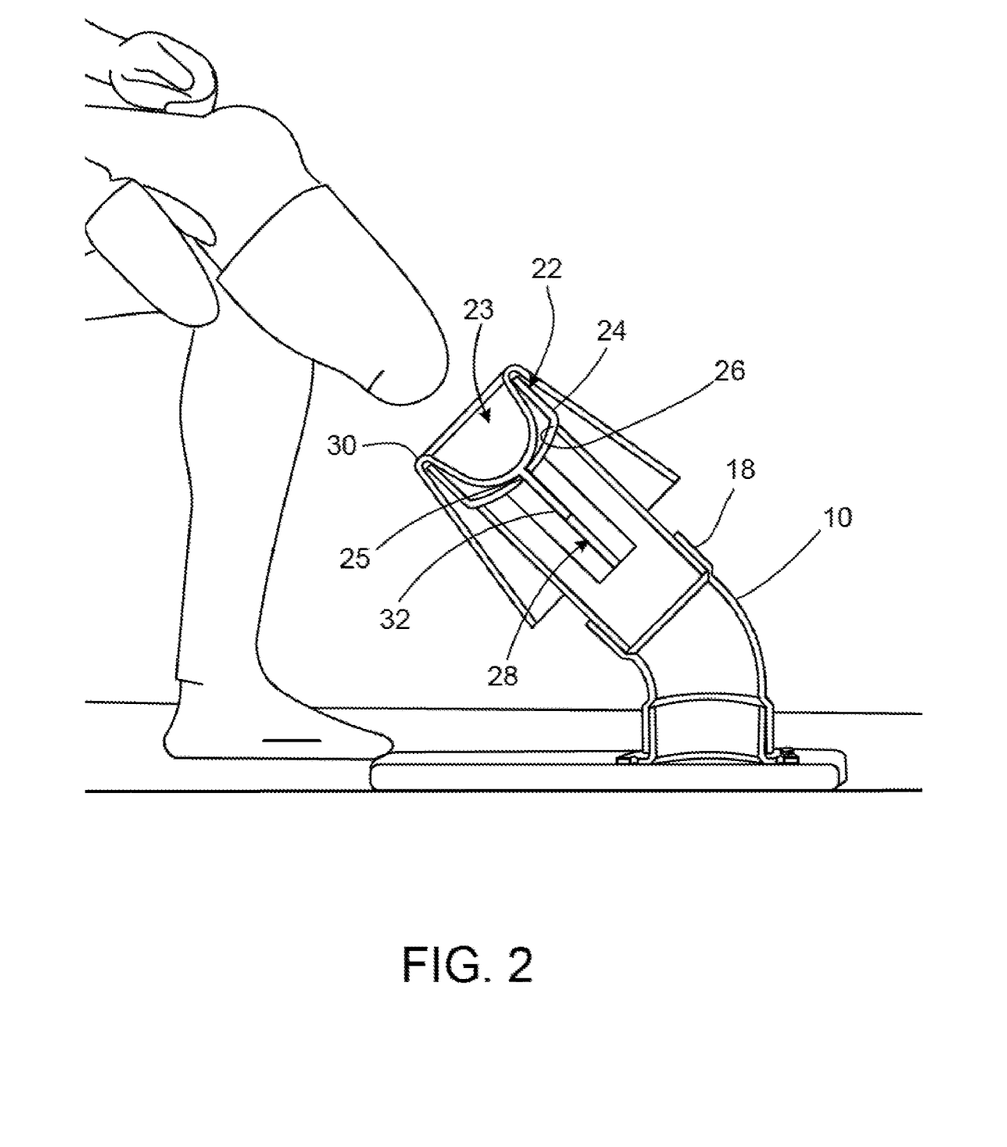
FIG. 2 is a cross sectional view of the alignment device of FIG. 1.

Referring to FIG. 2, which shows the alignment device 10 in cross section, the cup 22 has a cup-like shape, with a generally cylindrical wall 24 and a curved bottom. The wall 24 defines an inner wall surface 26 that defines the liner-receiving recess 23. The inner wall surface 26 also defines a liner pin-receiving guide hole 25 to a liner pin-receiving pin guide aperture 28 generally at its center and axially aligned along its longitudinal axis with the angled portion 18 of the alignment device 10. The axis of the cylindrical wall 24 is parallel to the pin guide aperture 28, e.g. the inner wall surface 26 of the cup 22 defining the liner-receiving recess 23 and the guide hole 25 to the liner pin-receiving aperture 28 have a common axis. The cup 22 is mounted to and extends generally from the cylindrical walls 24 of the angled portion 18. The angled portion 18 defines a hollow pin guide aperture 28. The pin guide hole 25 is aligned with the pin guide aperture 28 such that the liner pin 32 can easily fit through the pin guide hole 25 and extend into pin guide aperture 28.

Figure 3:
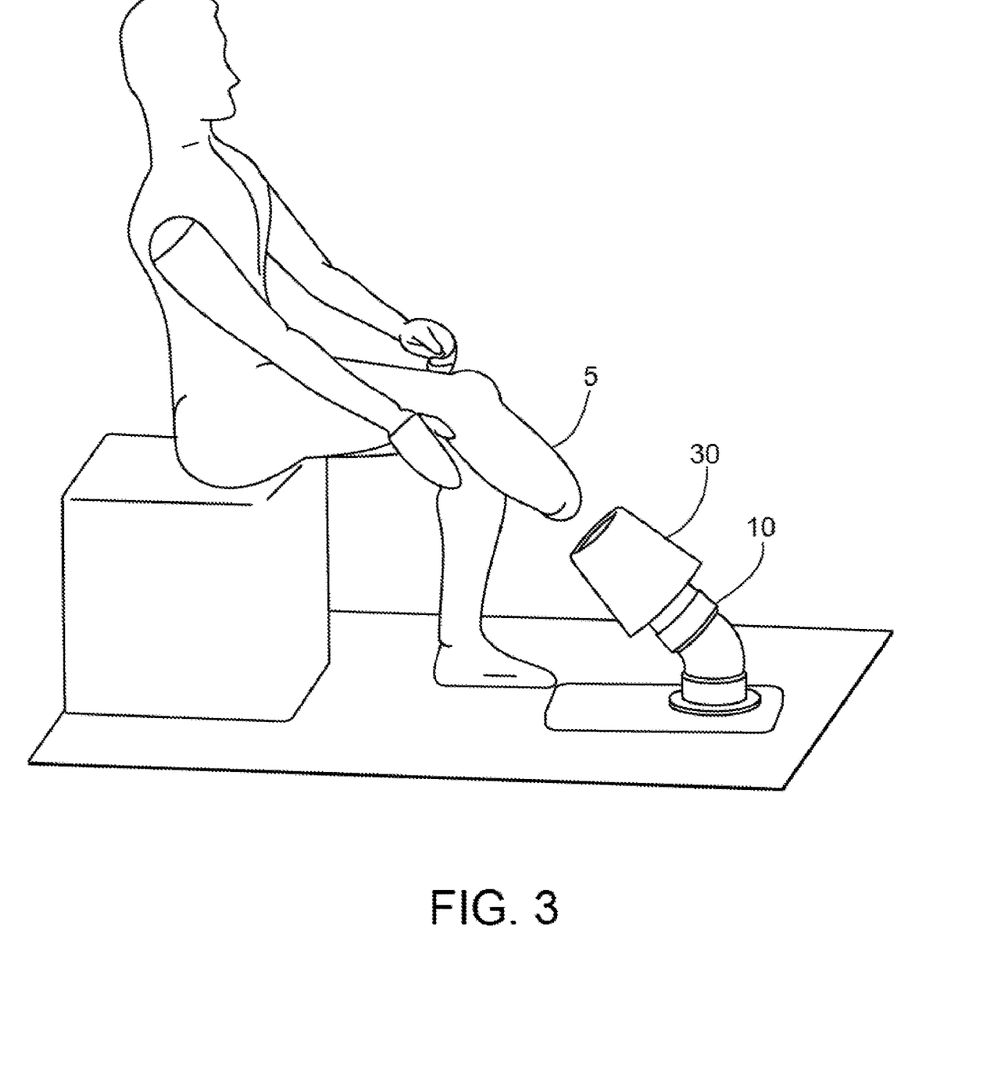
FIGS. 3-8 are somewhat schematic, cross sectional views sequentially showing a method for using the alignment device of FIG. 1.
Figure 4:
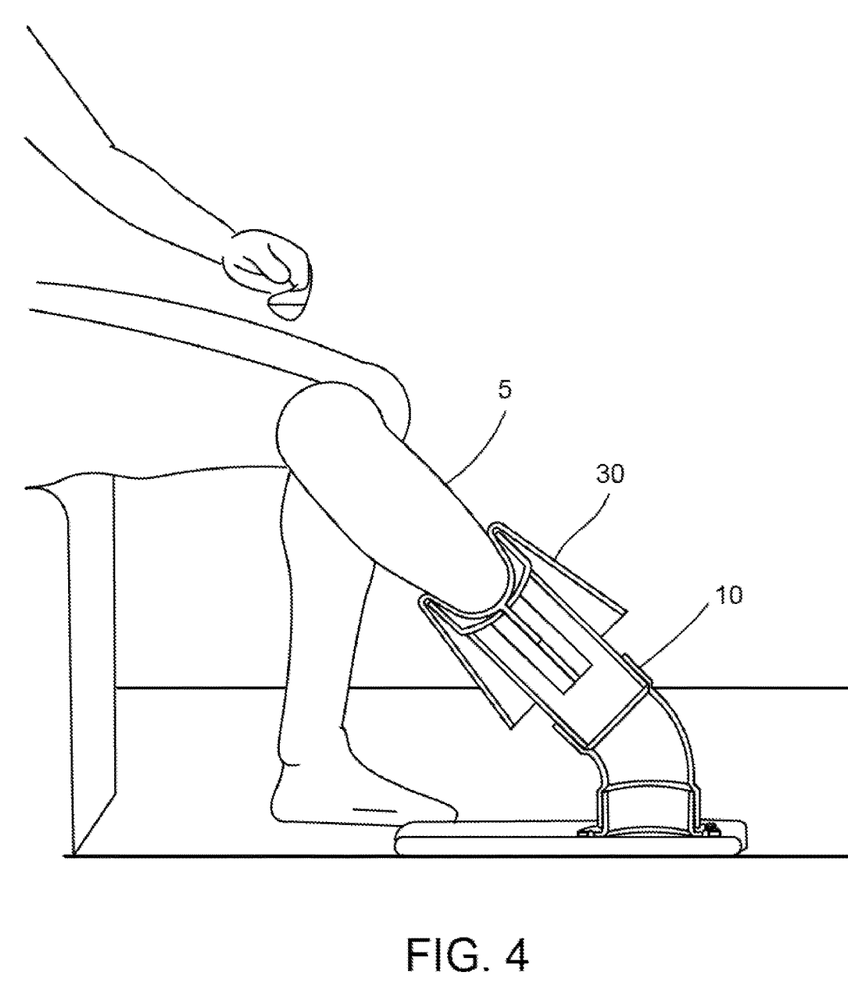
Figure 5:
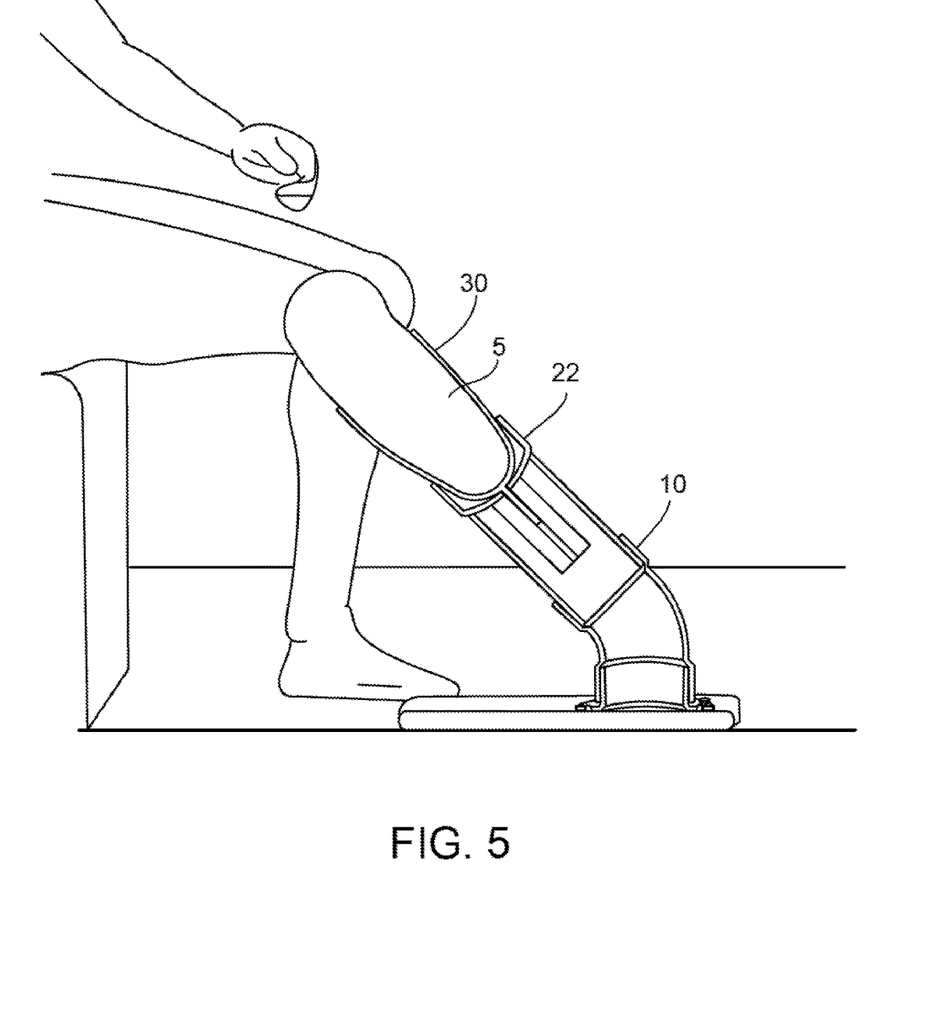
Figure 6:
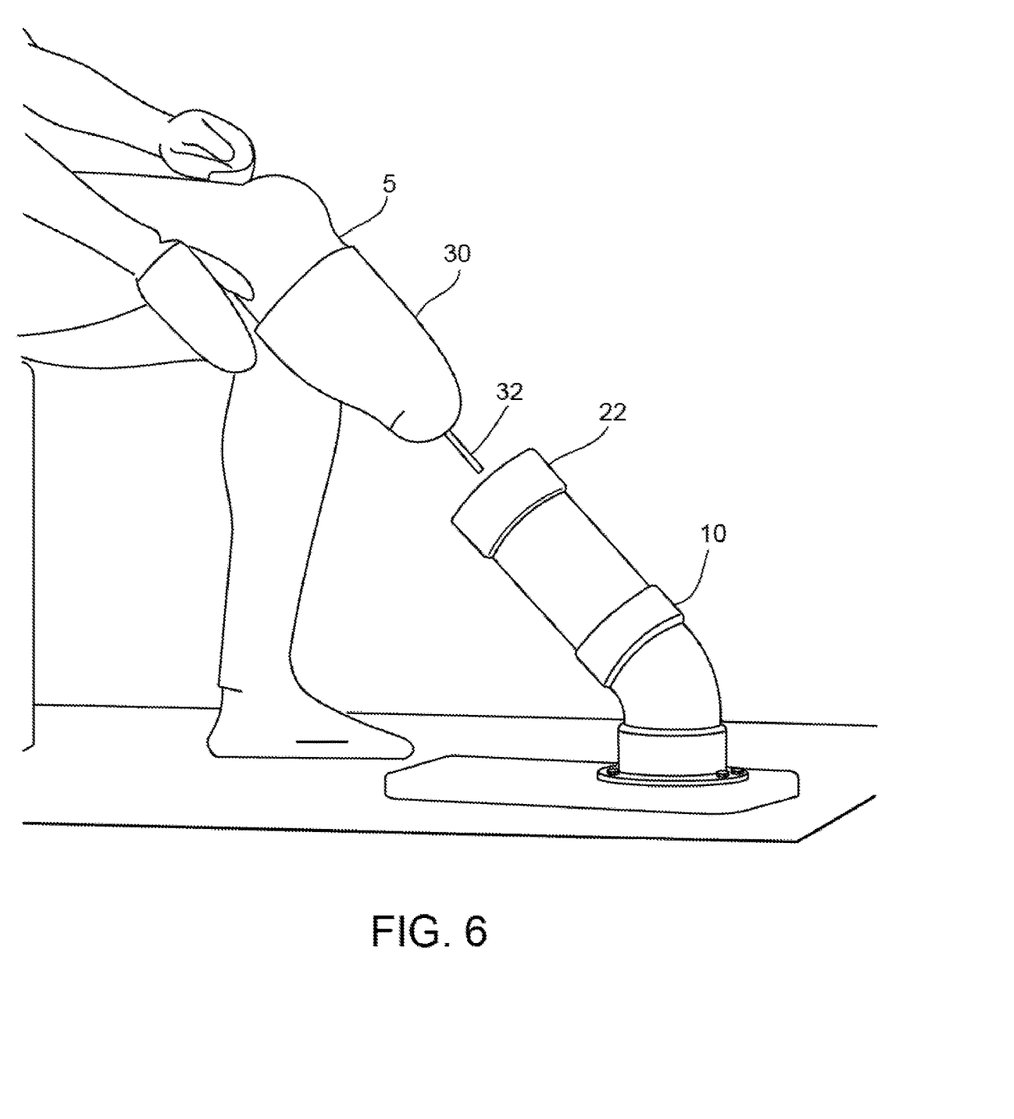
Figure 7:
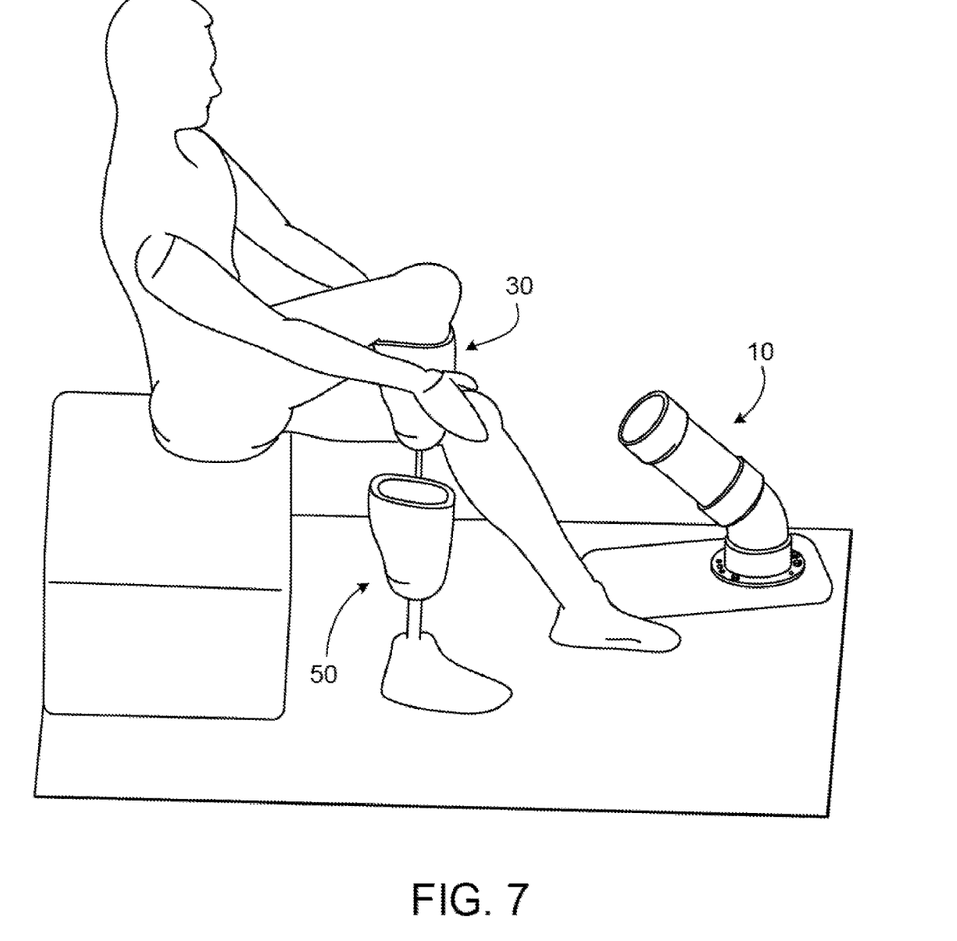
Figure 8:
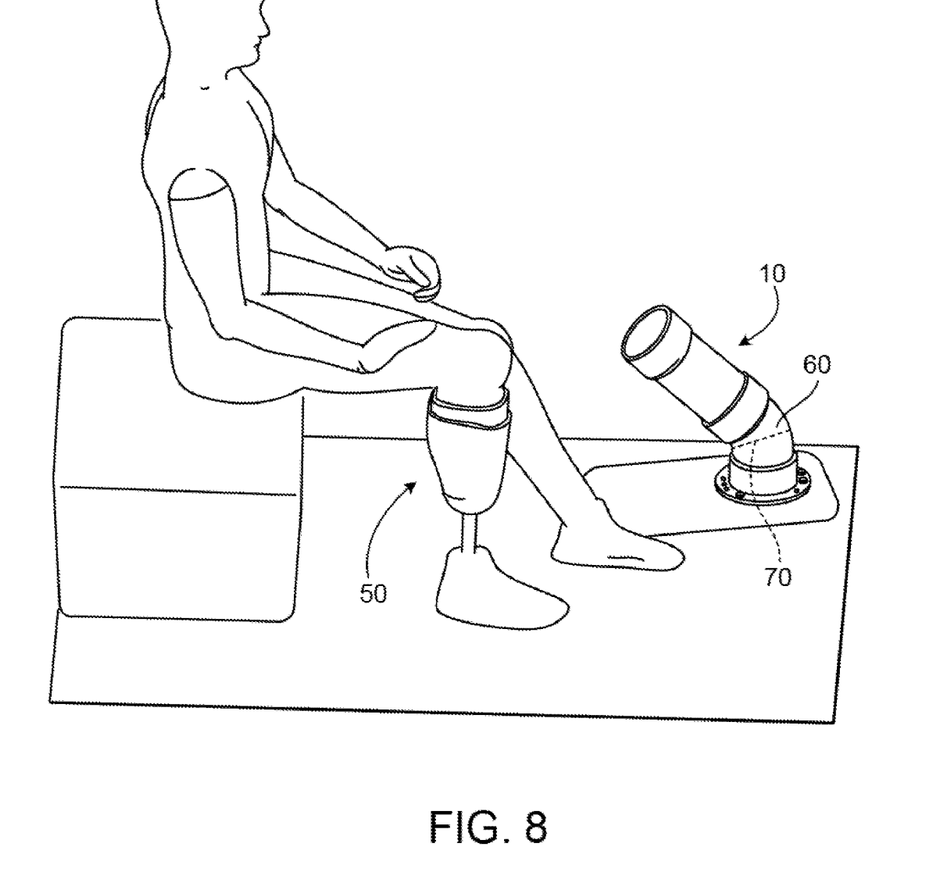

Referring also to FIG. 3, in preparation for donning the liner 30, the amputee inserts the liner pin 32 through the pin guide hole 25 and into pin guide aperture 28. The liner 30 is positioned in the cup 22 with attached liner pin 32 inserted into the alignment device 10 through the pin guide hole 25 and pin guide aperture 28. The upper portion of liner 30 is then rolled back over the outside of the cup 22, into a "ready" position. The amputee, while sitting on a chair or bed, then inserts the distal end of the leg stump 5 into the liner 30 resting in the cup 22 (FIG. 4). The upper portion of the liner 30 can then be rolled up onto the leg stump 5 (FIG. 5), while the alignment device holds the pin 32 coaxially aligned with the leg stump 5, greatly simplifying the process while reducing or eliminating the presence (and discomfort) of trapped air between the liner and stump. The leg stump 5, with the attached liner 30 and liner pin 32 secured in proper alignment, is then removed from the cup (FIG. 6), and the liner pin 32 in inserted into a prosthetic leg 50 in alignment (FIGS. 7 and 8). Since the pin has been aligned properly through use of the alignment device 10, the pin connects easily to the prosthetic leg. In practice, it has been found that the entire process can take less than, e.g., 30 seconds to complete.

Referring again to the Figures, the axis of the cylindrical walls 24 defining the liner recess 23 is parallel to the pin guide hole 25 to the pin guide aperture 28, e.g. coaxial. The lip 40 of the cup 22 defines a plane, P, lying perpendicular to the common axis of the recess and guide hole. In one implementation, the cup 22 has an inside diameter of approximately 4.5 inches and depth to the curved bottom surface 26 of approximately 2.75 inches, which accommodates most amputated leg stumps. The center of the cup top plane of one suitable implementation is approximately 14 inches from the floor surface. The pin guide hole 25 is approximately ⅜ inch in diameter and 4 inches long, in order to easily accommodate a prosthetic leg suspension liner pin. The angle of the pin guide with respect to the floor surface is typically in the ranges of 0 and 90 degrees, e.g. 45 degrees. Suitable materials for the cylindrical guide 14 of the alignment device 10 include PVC plastic, with a wood base 12. In one implementation, the alignment device weighs approximately nine pounds. The device can be made more portable, e.g., by simplifying the support structure and/or by selection of other suitable materials or arrangements.

A number of embodiments of the invention have been described. Nevertheless, it will be understood that various modifications may be made without departing from the spirit and scope of the invention. For example, although the alignment device has been described as a fixed structure, the height and/or angle of the alignment device could be made adjustable by any means known in the art, e.g. by means of a flexible (accordion type) elbow 60 (FIG. 8), by means of a pair of co-rotating, cooperative elbow elements (indicated by dashed line) 70 (FIG. 8), etc., to accommodate the height or sitting elevation of a range of individuals and/or seating surfaces.

Figure 9:
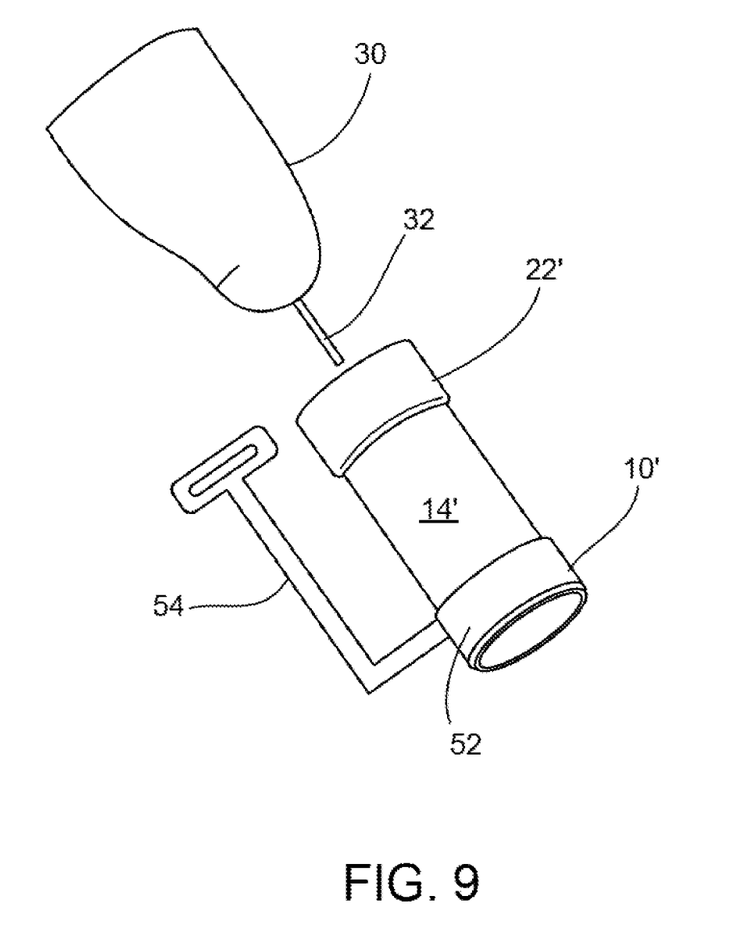
FIG. 9 is a somewhat schematic view of another implementation of an alignment device of this disclosure in which the support has the form of a handle.

Also, in another implementation of a prosthetic liner and liner pin alignment device of the disclosure, referring to FIG. 9, the device 10' may have a support in the form of an L-shaped handle 50 offset parallel to and attached at the distal end 52 of the body 14', i.e. instead of a base (e.g. base 12, FIG. 1). In this implementation, a user would place the liner pin in the liner pin aperture and fold the liner back onto the body 14'. Then, the handle 52 with either hand, the user would hold the body out and place their stump into the recess cup 22' and, using their other hand, roll the liner onto their leg. This handle 50 would thus replace the base, making it more portable, lighter weight, easier to store, etc.

Figure 10A:
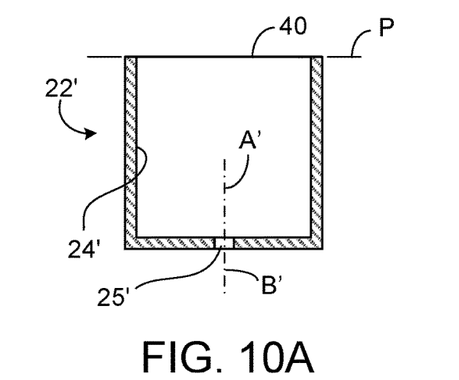
FIGS. 10A and 10B are somewhat diagrammatic side section and top views, respectively, of a first configuration of the axis of a liner-receiving recess defined by a cup and the axis of a pin guide hole defined by the cup.
Figure 10B:
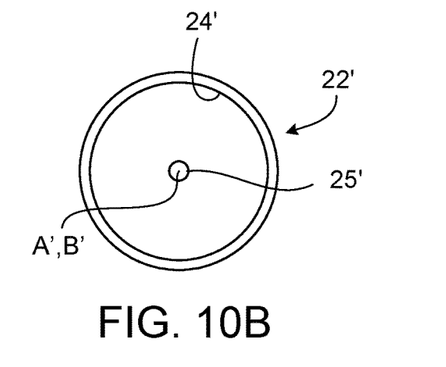
Figure 11A:
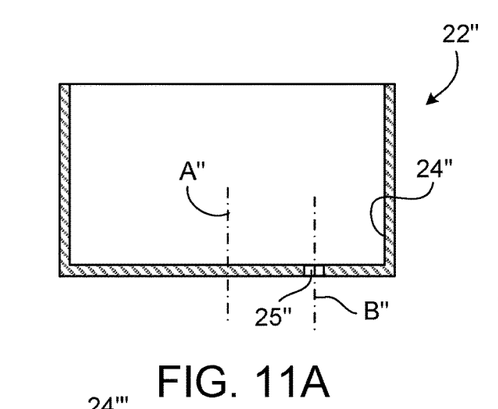
FIGS. 11A and 11B are somewhat diagrammatic side section and top views, respectively, of a second configuration of the axis of the liner-receiving recess and the axis of a pin guide hole.
Figure 11B:
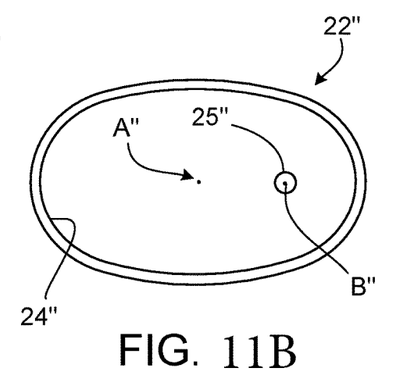
Figure 12A:
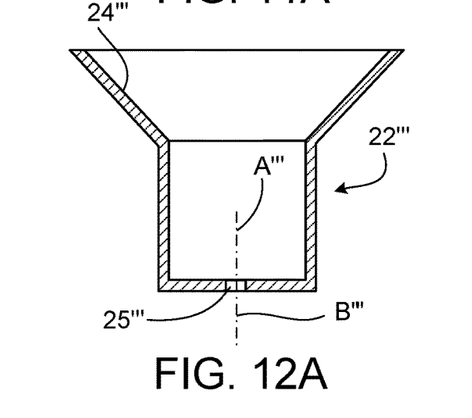
FIGS. 12A and 12B are somewhat diagrammatic side section and top view, respectively, of a third configuration of the axis a liner-receiving recess and the axis of the pin guide hole.
Figure 12B:
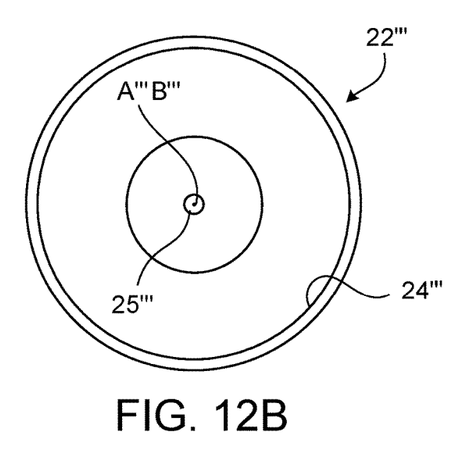

In implementations of the disclosure, the liner-receiving recess defined by the cup 22' and the pin guide hole 25' defined by the cup may, e.g., have a common axis, A', B', with a parallel wall 24' (FIGS. 10A and 10B); or the liner-receiving recess defined by the cup 22" and the pin guide hole 25" defined by the cup may, e.g., have non-common but parallel axes A", B", with a parallel wall 24" (FIGS. 11A and 11B); or the liner-receiving recess defined by the cup 22''' and the pin guide hole 25''' defined by the cup may, e.g., have common axes A''', B''', with a wall 24''' that is at least partially non-parallel (FIGS. 12A and 12B). Other arrangements may also be implemented.

Accordingly, other embodiments are within the scope of the following claims.

What is claimed is:

1. A method comprising:

positioning an alignment and positioning tool body at a predetermined angle relative to an alignment and positioning tool body base, in which the alignment and positioning tool body comprises a proximal cup having an inner wall surface defining a prosthetic leg liner receiving recess having a longitudinal tool axis, the alignment and positioning tool body defines, within the receiving recess, a prosthetic leg liner pin guide aperture having an open end of the aperture on the inner wall surface of the receiving recess, wherein the pin guide aperture and the open end of the pin guide aperture are in communication with the receiving recess and have a central axis parallel to the longitudinal tool axis, and wherein the prosthetic leg liner receiving recess has a depth to width ratio of less than one;

inserting a prosthetic leg suspension liner pin of a prosthetic leg suspension liner into the open end of the prosthetic leg liner pin guide aperture of the prosthetic leg liner receiving recess defined by the inner wall surface of the proximal cup of the alignment and positioning tool body;

positioning the prosthetic leg suspension liner pin within the prosthetic leg liner pin guide aperture;

aligning the prosthetic leg suspension liner pin with the longitudinal tool axis;

rolling an upper portion of the suspension liner over outside of the proximal cup; and inserting a distal end of a leg stump into the suspension liner resting in the proximal cup, rolling up the upper portion of the suspension liner onto the leg stump while using the alignment and positioning tool body to hold the suspension liner pin coaxially aligned with the leg stump.

2. The method of claim 1 in which the prosthetic leg liner pin guide aperture is approximately ⅜ inch in diameter and four inches long.

3. The method of claim 1 in which the longitudinal tool axis and the central axis are coaxial.

4. The method of claim 1 in which the cup defines a proximal lip opening to the prosthetic leg liner receiving recess, with the proximal lip opening lying perpendicular to the central axis of the prosthetic leg liner pin guide aperture.

5. The method of claim 1 in which the predetermined angle of the alignment and positioning tool body to the alignment and positioning tool body base is in the range of 0 degrees to 90 degrees.

6. The method of claim 5 in which the predetermined angle is about 45 degrees.

7. The method of claim 1 in which the alignment and positioning tool body, in at least a region of the prosthetic leg liner receiving recess, is cylindrical and defines an outer surface sized and shaped to receive there-over a portion of a prosthetic leg liner extending from the recess.

8. The method of claim 1 in which the alignment and positioning tool body is cylindrical.

9. The method of claim 1, comprising adjusting the predetermined angle.

10. The method of claim 1 in which the alignment and positioning tool body support comprises a handle.

11. The method of claim 1 in which at least a portion of the inner wall surface defining the prosthetic leg liner receiving recess lies parallel to the longitudinal axis.

12. The method of claim 1 in which at least a portion of the inner wall surface defining the prosthetic leg liner receiving recess lies perpendicular to the longitudinal axis.

13. The method of claim 1 in which at least a portion of the inner wall surface defining the prosthetic leg liner receiving recess lies parallel to the central axis.

14. The method of claim 1 in which the pin guide aperture has a length-to-width ratio greater than 10.

15. A method comprising:
inserting a liner pin of a prosthetic leg suspension liner into an open end of a prosthetic leg liner pin guide aperture of a prosthetic leg liner receiving recess defined by an inner wall surface of a proximal cup of an alignment and positioning tool body,
wherein the alignment and positioning tool body comprises:
a vertical tool body support portion, and
an angled tool body support portion comprising:
the proximal cup having the inner wall surface defining the receiving recess having a longitudinal tool axis, and
the pin guide aperture having the open end of the aperture on the inner wall surface of the receiving recess, in which the pin guide aperture and the open end of the aperture are in communication with the receiving recess and have a central axis parallel to the longitudinal tool axis,
wherein the receiving recess has a depth to width ratio of less than one;
connecting the vertical tool body support portion to the angled tool body support portion at an angle of approximately 45 degrees;
connecting a flat base to the vertical tool body support portion of the alignment and positioning tool body;
positioning the prosthetic leg suspension liner pin within the prosthetic leg liner pin guide aperture;
aligning the prosthetic leg suspension liner pin with the longitudinal tool axis;
rolling an upper portion of the suspension liner over outside of the proximal cup; and
inserting a distal end of a leg stump into the suspension liner resting in the proximal cup, rolling up the upper portion of the suspension liner onto the leg stump while using the alignment and positioning tool body to hold the suspension liner pin coaxially aligned with the leg stump.

16. The method of claim 15 in which the pin guide aperture and the open end of the aperture together are approximately ⅜ inch in diameter and four inches long.

17. The method of claim 15 in which the pin guide aperture has a length-to-width ratio greater than 10.

18. A method comprising:
inserting a prosthetic leg liner pin that is attached to a prosthetic leg liner into a receiving pin guide aperture defined within a prosthetic leg liner receiving recess defined by an inner wall surface of a proximal cup of an alignment and positioning tool body,
wherein the prosthetic leg liner receiving recess has a longitudinal tool axis and a depth to width ratio of less than one,
wherein the alignment and positioning tool body defines, within the receiving recess, the receiving pin guide aperture lying in communication with the receiving recess and having a central axis parallel to the longitudinal tool axis;
positioning the prosthetic leg liner pin within the prosthetic leg liner pin guide aperture;
aligning the prosthetic leg liner pin with the longitudinal tool axis;
rolling an upper portion of the prosthetic leg liner over outside of the proximal cup;
inserting a distal end of the leg stump into the prosthetic leg liner resting in the proximal cup; and
rolling up the upper portion of the prosthetic leg liner onto the leg stump while using the alignment and positioning tool body to hold the prosthetic leg liner pin coaxially aligned with the leg stump.

19. The method of claim 18 in which the prosthetic leg liner pin guide aperture is approximately ⅜ inch in diameter and four inches long.

20. The method of claim 18 in which the pin guide aperture has a length-to-width ratio greater than 10.

21. The method of claim 18 in which the longitudinal tool axis and the central axis are coaxial.

22. The method of claim 18 in which the proximal cup defines a proximal lip opening to the prosthetic leg liner receiving recess, with the proximal lip opening lying perpendicular to the central axis of the receiving pin guide aperture.

* * * * *